(12) United States Patent
Cagran et al.

(10) Patent No.: US 9,703,022 B2
(45) Date of Patent: Jul. 11, 2017

(54) DEFLECTING PRISM AND MEASURING ASSEMBLY

(71) Applicant: ANTON PAAR GMBH, Graz-Strassgang (AT)

(72) Inventors: Claus Cagran, Graz (AT); Michael Imre, Graz (AT); Ulrich Heppner, Graz (AT)

(73) Assignee: Anton Paar GmbH, Graz-Strassgang (DE)

( * ) Notice: Subject to any disclaimer, the term of this patent is extended or adjusted under 35 U.S.C. 154(b) by 38 days.

(21) Appl. No.: 14/682,270

(22) Filed: Apr. 9, 2015

(65) Prior Publication Data

US 2015/0293274 A1  Oct. 15, 2015

(30) Foreign Application Priority Data

Apr. 9, 2014 (AT) .............................. A 50266/2014

(51) Int. Cl.

| G01N 21/41 | (2006.01) |
|---|---|
| G02B 5/04 | (2006.01) |
| G02B 1/02 | (2006.01) |
| G01N 21/552 | (2014.01) |
| G01J 1/04 | (2006.01) |
| G01N 21/43 | (2006.01) |

(52) U.S. Cl.
CPC .............. *G02B 5/04* (2013.01); *G01J 1/0477* (2013.01); *G01N 21/43* (2013.01); *G01N 21/552* (2013.01); *G02B 1/02* (2013.01); *G01N 2021/434* (2013.01); *G01N 2201/068* (2013.01)

(58) Field of Classification Search
CPC .... G01N 21/4133; G01N 21/43; G01N 21/41; G01N 21/431; G01N 21/552; G01N 21/553; G01N 2021/434; G01N 2136/34; G02B 5/04; G01J 1/0477
USPC ......... 356/237.1–237.5, 239.1, 239.2, 239.7, 356/239.8, 73, 301
See application file for complete search history.

(56) References Cited

U.S. PATENT DOCUMENTS

| 2,305,777 | A | * | 12/1942 | Hansen | .................. | G01N 21/43 |
| | | | | | | 356/136 |
| 2,807,976 | A | * | 10/1957 | Vossberg | ............... | G01N 21/43 |
| | | | | | | 250/235 |
| 4,803,470 | A | * | 2/1989 | Fineman | ................ | G08B 19/02 |
| | | | | | | 340/583 |
| 6,535,283 | B1 | * | 3/2003 | Heffels | .............. | G01N 21/8507 |
| | | | | | | 250/341.8 |

(Continued)

*Primary Examiner* — Hoa Pham
(74) *Attorney, Agent, or Firm* — Laurence A. Greenberg; Werner H. Stemer; Ralph E. Locher

(57) ABSTRACT

A deflecting prism for electromagnetic radiation, in particular for refractometer- and/or ATR-measurements, is part of a measuring configuration. The deflecting prism has a body produced in one piece from a mono-crystal. The body has at least two beam conductive surfaces on a side of the body opposite each other or circumferentially about the body and a measuring surface lying between the beam conductive surfaces or surrounded by the latter. The body further has at least one beam entry surface or a beam exit surface. Accordingly, the measuring surface lies on an elevation formed on the body, which crosses over via a ledge surrounding the elevation into the remaining part of the body. On the remaining part, the beam conductive surfaces and/or the beam entry surface or exit surface lie.

20 Claims, 3 Drawing Sheets

(56) References Cited

U.S. PATENT DOCUMENTS

| | | | | |
|---|---|---|---|---|
| 7,349,092 B1* | 3/2008 | Tiwald | ............... | G01N 21/0303 |
| | | | | 356/135 |
| 8,081,305 B2* | 12/2011 | Azimi | ....................... | G01J 3/02 |
| | | | | 250/339.08 |
| 2012/0081698 A1* | 4/2012 | Christian | ............... | G01N 21/43 |
| | | | | 356/128 |
| 2013/0275052 A1* | 10/2013 | Loder | .................... | G01N 21/59 |
| | | | | 702/24 |
| 2014/0374601 A1* | 12/2014 | Pastore | .............. | G01N 21/3563 |
| | | | | 250/341.1 |

* cited by examiner

DEFLECTING PRISM AND MEASURING ASSEMBLY

CROSS-REFERENCE TO RELATED APPLICATION

This application claims the priority, under 35 U.S.C. §119, of Austrian application A50266/2014, filed Apr. 9, 2014; the prior application is herewith incorporated by reference in its entirety.

BACKGROUND OF THE INVENTION

Field of the Invention

The invention relates to a deflecting prism for electromagnetic radiation according to the preamble of the main patent claim. Such prisms are used particularly for the examination of fluids, in particular, in attenuated total reflections (ATR) measuring devices or refractometers. It is of special importance thereby, that the deflecting prism is used as an optical element of a measuring device or a measuring arrangement hermetically sealed into the housing of the measuring device or into the housing wall of a pipeline conducting the medium to be examined.

Such deflecting prisms and measuring devices are needed in different process applications in the food industry, in the chemical industry, in the paper industry, etc. and are used for the identification or measured value collection of or in process fluids, in particular process liquids. Examples for this are absorption measurements with ATR crystals and, for example, $CO_2$ sensors, wherein the density of the fluids or their existing quantity can be inferred from the absorption of characteristic wave lengths in the infrared range. Also, the measurement of the critical angle of the total reflection in refractometers is made with such deflecting prisms.

In both cases electromagnetic radiation is guided from a source into the deflecting prism and is totally reflected on a boundary surface or measuring surface towards the medium to be examined depending on the angle of incidence and refractive index difference between the deflecting prism and the fluid to be examined. The intensity of the reflected light is measured with a detector configured for the respective type of problem. Depending on the parameters of the fluid to be examined, a change of the angle of the total reflection or the intensity of the total reflected light occurs, which measured value is consulted for the determination of the parameters of the examined fluids.

Difficulties arise in the installation of the deflecting prism in the housing wall or the pipelines in that a soldering must be performed for the gas-tight connection of the deflecting prism with the housing wall or pipe wall. The walls consist in the process applications, as a rule, of stainless steel or titanium and, if need be, also of ceramic materials, which have sufficient hardness and chemical resistance to the media to be examined. Furthermore, sanitary regulations must also be observed, in particular, that the media may not escape through unsealed solder joints from the sample line or that no gaps or bumps are present at all, in which bacteria could concentrate.

The use of elastic seals or of rigid seals, for example, made of Teflon have not proven advisable particularly due to the maintenance costs, the material aging and for cleaning reasons. Preferably, therefore, in practice the connections between such deflecting prisms and the pipe-wall or housing wall should be made by soldering. For example, sapphire crystals can be soldered into a wall by gold-solder or platinum solder. Such solder joints are, however, difficult to carry out particularly for mono-crystals, particularly if the measuring surface is supposed to be connected flatly level with the outer wall surface of the measuring device or with the inner wall surface of the pipeline, in order to satisfy, for example, hygienic standards for applications in the food sector. In addition, the solder joint should be hermetically sealed gas-tight over the service life of the measuring device. Here, in particular, the different expansion coefficients of stainless steel and crystals and soldering material must be taken into consideration. In particular, leaks occur time and again due to chippings of the crystal, which often do not resist the pressures and stresses which occur. In particular, in the case of soldering it should also be ensured that the soldering temperature is kept as low as possible, which is why for the most part eutectics of the soldering materials employed are used as soldering materials.

It was found that the outer form of the deflecting prisms in the area of the solder joint plays an important role, in order to impart to the mono-crystal employed the necessary resistance to the temperatures occurring during the soldering and in the operation and sufficient stability under stresses.

SUMMARY OF THE INVENTION

According to the present invention, a deflecting prism of the type mentioned at the outset is characterized by the features cited in the characterizing part of the main claims. It is provided, that the measuring surface lies on an elevation formed on the body, which via a ledge surrounding the elevation crosses over into the remaining part of the body, on which remaining part the beam conductive surface(s) and/or beam entry surface(s) or beam exit surface(s) lie.

Thus, the soldering is done in an area of the body of the prism, which is specially configured. The elevation formed on the body of the prism is used for accommodating the solder joint, wherein in turn the solder joint not completely, but rather only partially surrounds the circumference of the elevation, specifically in the area facing the measuring surface or abutting against the latter. It was shown that the soldering of the mono-crystal prisms into housing walls or pipelines, in particular, in the use of eutectic soldering materials, can thus be undertaken without damaging the mono-crystal. Furthermore, measuring devices with such soldered crystals showed an extremely long service life, without leaks developing or damages at the solder joint or at the crystal.

It is advantageous for the production of the deflecting prism and also for the use in measuring devices, if the measuring surface and the beam entry surface or beam exit surface are formed by level surfaces aligned parallel to each other and/or if the end surface of the elevation constitutes a measuring surface.

It is advantageous for the stability and production of the deflecting prism, if the body and/or the elevation are configured centrally symmetrically with respect to an axis perpendicular to the measuring surface and/or if the measuring surface and/or the body and/or the elevation have at least two symmetry planes running perpendicular to the measuring surface and/or if the elevation has a cylindrical, truncated cone-shaped or truncated pyramid-shaped form or the form of a rectangular cuboid with a regular polygonal base.

In order to improve the mechanical strength of the mono-crystal used for the prism, it can be provided, that the crossover edge of the ledge of the elevation to the remaining part of the body or to a contact surface formed on the remaining part of the body, surrounding the elevation, is configured rounded and/or conical.

It is advantageous, if the height of the elevation in relation to the contact surface or the remaining part of the body and/or the width of the contact surface are selected so that the crossover edge does not influence the measuring beam path or lies outside the measuring beam path.

The height and width ratio is thus selected such that the entry and exit angle of the measuring beam desired for the respective measuring application can be realized on the measuring surface of the prism in combination with the angle of the circumferential beam conductive surface and the entry and exit surfaces.

For the soldering behavior of the mono-crystal used it has been shown that it is advantageous, if the elevation has at least a circumferential surface, which departs from the measuring surface inclined outwards and with the contact surface contains an angle A of 45°≤A≤90°, preferably 70°≤A≤90°, wherein the angle A opens to the interior of the elevation.

For the production and the application behavior it is advisable, if the contact surface runs parallel to the measuring surface.

A special form of a deflecting prism is characterized in that the remaining part of the body is formed at least partially from a rotation body, for example, spherical segment or ellipsoid segment or—sector and the beam conductive surfaces are formed from the circumferential surface or parts or the circumferential surface of the rotation body.

A measuring arrangement according to the present invention has a deflecting prism. The deflecting prism is soldered into a wall of the measuring device which can be brought into contact with the medium to be examined or a pipeline conducting the medium to be examined and the measuring surface of the deflecting prism can make contact with the medium. The deflecting prism is characterized according to the present invention in that the solder joint of the body of the prism only surrounds the elevation and proceeding from the circumferential edge of the measuring surface extends over maximally 70%, preferably maximally 60% of the height of the elevation.

By the limiting of the solder joint to the edge of the elevation near to the medium it was achieved, that damage to the mono-crystal during the soldering is largely prevented and also in operation the service life of the mono-crystal is considerably increased.

It is also advantageous if the inner wall section of the wall connecting to the solder joint has a distance to the circumferential surface of the elevation, which exceeds the thickness of the solder joint between the elevation and the inner wall section. It is thereby prevented that during the thermal expansion the housing wall and the deflecting prism come in contact, whereby damages are prevented.

An improvement for the soldering process and the tightness results, if the distance between at least one sub-area of the inner wall section of the wall forming the solder joint has a distance to the at least one circumferential surface of the elevation, which at least in sections continuously increases towards the measuring surface.

It can be provided for improving the solderability and improved application of the soldering material, that in the area of the solder joint a layer made of titanium or gold or alloys of these metals is applied to the circumferential surface of the elevation, which has a size of less than 100 μm preferably less than 20 μm, on which the solder layer is applied.

In order to prevent damages to the mono-crystal due to thermal expansions or thermal stresses in the housing or in the housing wall, it can be provided, that the deflecting prism and a housing of the measuring device or pipeline having the wall with a recess for the deflecting prism or with the inner wall section are exclusively connected via the solder joint.

In order to facilitate the soldering, it can be provided, that the thickness of the solder joint or the distance between the circumferential surface of the elevation and the inner wall section of the measuring surface increases towards the contact surface.

Other features which are considered as characteristic for the invention are set forth in the appended claims.

Although the invention is illustrated and described herein as embodied in a deflecting prism and a measuring assembly, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
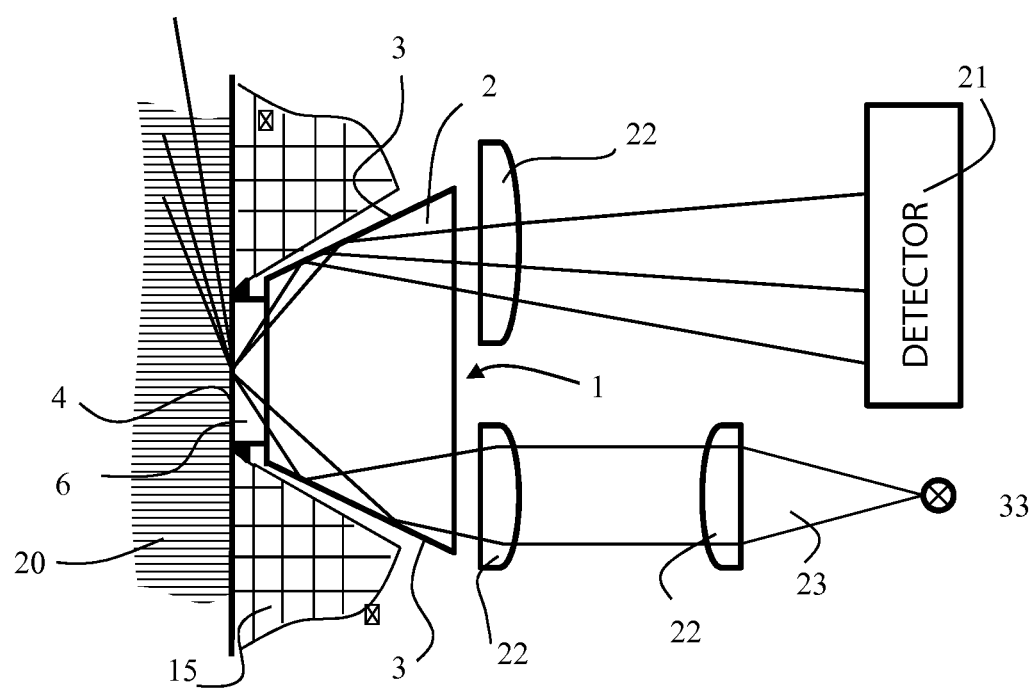
FIG. 1 is an illustration showing schematically a measuring device according to the invention.
Figure 2A:
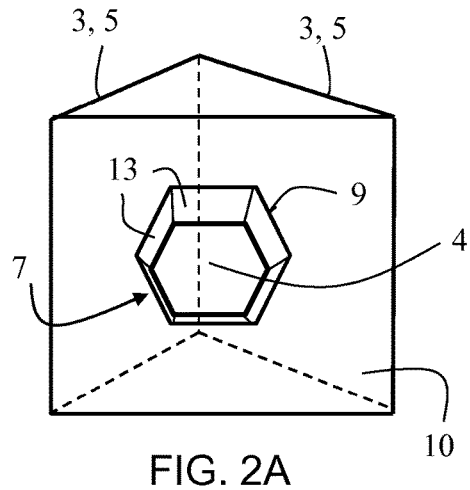
FIGS. 2A-2D are diagrammatic, perspective views showing different forms of a deflecting crystal.
Figure 2B:
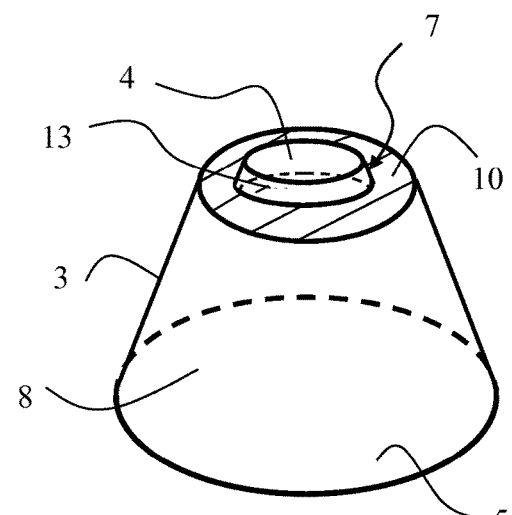
Figure 2C:
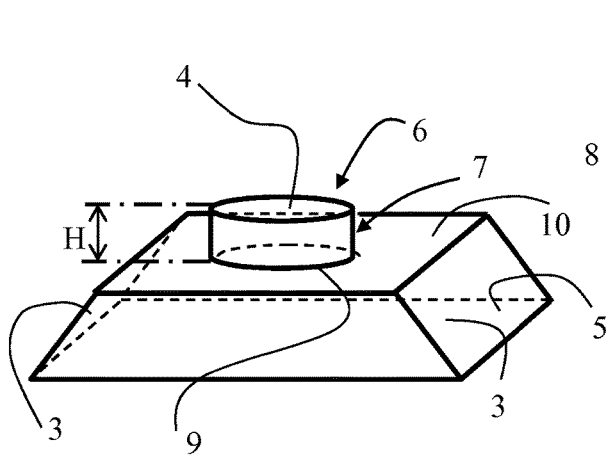
Figure 2D:
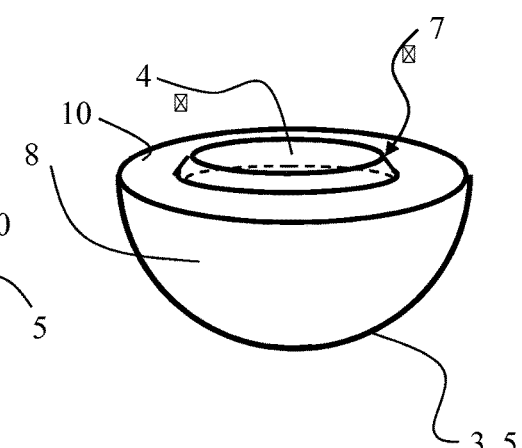

Referring now to the figures of the drawings in detail and first, particularly to FIG. 1 thereof, there is shown a principle structure of a measuring device according to the present invention, in this case of an Abbe-refractometer for measuring a critical angle of a total reflection. A deflecting prism 1 is inserted tightly with its boundary surface or its measuring surface 4 against a medium 20 to be examined, which is located, for example, in a process pipe, in a recess 30 in a wall 15 of the process pipe. For the measurement, electromagnetic radiation 23 of predetermined wave lengths is radiated from a radiation source 33 into the deflecting prism 1, if necessary, via collimators 22. In addition, filters can also be installed in the beam path, in order to select or mask out targeted wave length ranges and/or polarization directions. The radiation 23 emanating from the radiation source 33 is radiated on the side-surfaces or beam surfaces 3 or the side media boundary surfaces of the deflecting prism 1. An angle of the impinging radiation 23, which contains this with the beam conductive surface 3, is thereby selected such that a total reflection of the incident radiation occurs on these beam conductive surfaces 3. The radiation 23 is reflected from the beam conductive surfaces 3 into an optical window or onto a measuring surface 4, which measuring surface 4 is in contact with the medium 20 to be examined. The radiation 23 impinging on the measuring surface 4 is totally reflected depending on an angle of incidence and a refractive index difference between the medium 20 and prism material on the boundary surface or measuring surface 4 and/or scattered into the medium 20. The portion of the radiation 23 remaining in the deflecting prism 1 is totally reflected via a further beam conductive surface 3 and arrives via further collimators 22 and, if need be, filters at a receiver or detector 21, which measures an arriving intensity of the radiation 23 reflected on the measuring surface 4. The measured values obtained are examined with regard to concentrations of media component parts and/or to the component parts or components of the medium 20.

A prerequisite for these measurements is that the deflecting prisms for such measurements have a higher refractive index than the medium to be examined.

The materials used for the deflecting prisms are as a rule sapphire, YAG and spinel. Other materials can also be used. They are consistently mono-crystalline or equivalently constructed bodies, which are formed or processed into a prism. It is stressed, that the term prism is understood to mean any body, which can totally reflect an incident electromagnetic radiation at least on the measuring surface, so that the radiation reflected on the measuring surface, if necessary, can be conducted over at least one additional beam conductive surface via at least one further total reflection to a receiver. The term "prism" does not hereby stand for the geometrical body, but rather for any body, which makes possible an appropriate beam deflection, just as exists in a prism.

Advantageously, the crystal used for such measurements has a form suitable for the measurement with the side-conductive surfaces or beam conductive surfaces 3 tapering towards the measuring surface 4 or approaching each other, which conduct the measuring beam 23 to the measuring surface 4. Examples for deflecting prisms, as they can be used during measurements, are depicted in FIGS. 2A-2D. Basically, the deflecting prisms 1—as also depicted—can be formed from prismatic bodies, truncated pyramid-shaped bodies, truncated cone-shaped bodies, etc., which can have corresponding symmetries. Also, rotation bodies like ellipsoids or hemispheres can be used with flattened, level end surfaces forming the measuring surface 4 and arbitrarily formed surfaces forming the beam entry- and exit surface 5. In this case the beam conductive surfaces 3 are formed from an inner wall surface of a rotation body. The inclined or curved surfaces or beam conductive surfaces 3 conduct the radiation 23 to the optical window or to the measuring surface 4 and ensure the appropriate angle of incidence there, in order either to bring about a total reflection or to be able to examine the measuring radiation with regard to the critical angle to the total reflection and/or to supply the portion of the measuring radiation 23 reflected on the measuring surface 4 to the detector 21 via the additional or opposite beam conductive surface 3. If necessary, the deflection via a beam conductive surface 3 can also be omitted and the measuring beam is guided directly to the measuring surface 4 at a predetermined angle.

It is evident from these figures, that circumferential surfaces 13 of an elevation 6 or a ledge 7 can be arranged perpendicular or inclined against a contact surface 10. The measuring surface 4 and the contact surface 10 are preferably configured parallel, but can, also be configured inclined to each other, particularly if the housing wall 15 touches the prism 1 only at the solder joint.

Figure 3A:
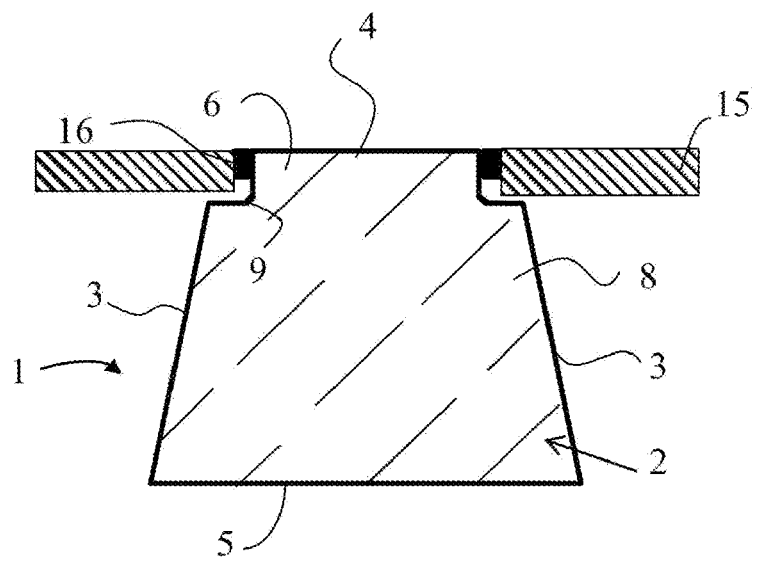
FIGS. 3A-3C are sectional views showing different possibilities for soldering of deflecting prisms into a wall of a housing of measuring devices.

FIG. 3A shows in a sectional view the body 2 of the deflecting prism 1, which is formed in a truncated cone-shaped manner and bears the cylindrical elevation 6. The cylindrical elevation 6 is soldered via a solder joint 16 into a recess 30 of the wall 15 of the housing of a measuring device or a pipeline. Reference numeral 8 shows a remaining part of the body 2. Reference numeral 9 shows a crossover edge 9 of the body 2.

Figure 3B:
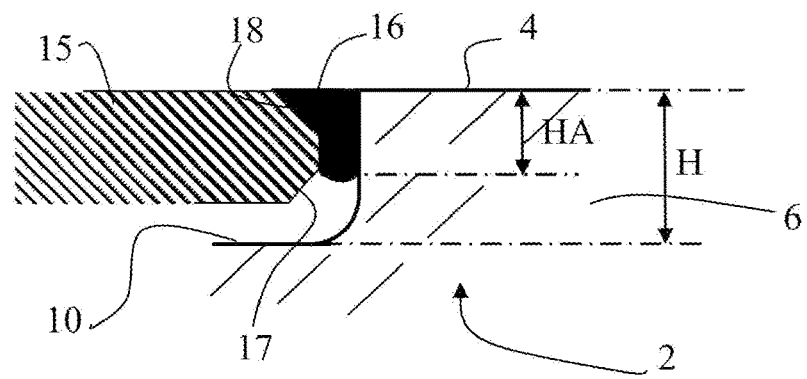

FIG. 3B shows the wall 15, which is beveled in the solder area at its end area facing the medium and the deflecting prism 1. A more uniform wetting of the solder area is thereby ensured with the solder; this is above all especially advantageous in respect to the formation of a gas-tight solder joint.

Figure 3C:
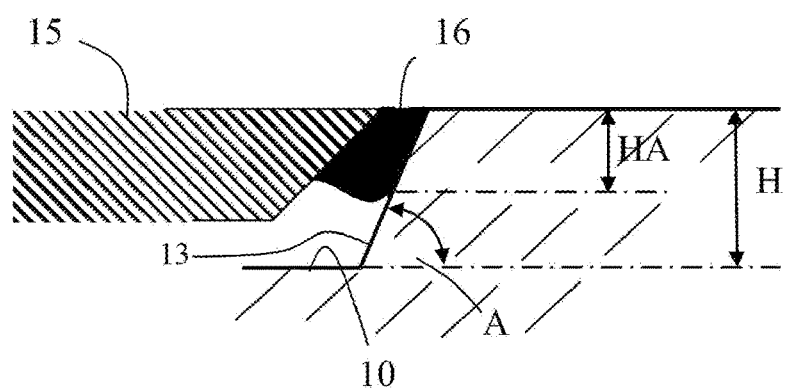

FIG. 3C shows the 15, which in the direction towards the body 2 diverges from the latter, so that the solder joint 16 widens in the direction towards the body 2.

At the same time the elevation 6 is limited here by a circumferential surface 13, which departs from the measuring surface inclined outwards and with the plane of the contact surface 10 contains an angle A of $45° \leq A \leq 90°$, preferably $70° \leq A \leq 90°$, wherein the angle A opens to the interior of the elevation 6.

In each case a height HA of the solder joint 16 does not extend in a direction perpendicular to the measuring surface 4 above the total height H of the elevation 6 in respect to the contact surface 10, but rather ends at a distance HA from the end surface of the elevation 6 or from the measuring surface 4. The distance HA is maximally 80% of the height H of the elevation 6.

The invention claimed is:

1. A measuring configuration, comprising:
   a deflecting prism for electromagnetic radiation and having a measuring surface:
   a measuring unit containing either:
      a measuring device having a wall with a recess formed therein, said deflecting prism soldered in said recess in said wall, said deflecting prism facing or can be brought into contact with a medium to be examined; or
      a pipeline having a wall, said deflecting prism soldered in said wall of said pipeline, and said measuring surface facing the medium or can make contact with the medium;
   said deflecting prism having a body formed in one piece from a mono-crystal, said body containing:
      sides with at least two beam conductive surfaces disposed opposite each other or circumferentially about said body;
      said measuring surface lying between said beam conductive surfaces or surrounded by said beam conductive surfaces;
      at least one beam conductive surface selected from the group consisting of a beam entry surface and a beam exit surface;
      a remaining part; and
      an elevation having a ledge surrounding said elevation, said measuring surface lying on said elevation formed on said body, said elevation crossing over via said ledge into said remaining part, and on said remaining part at least one of said beam conductive surfaces, said beam entry surface or said beam exit surface lies; and
   a solder joint surrounding only said elevation of said body of said deflecting prism and said solder joint proceeding from a circumferential edge of said measuring surface extends over maximally 80% of a height of said elevation.

2. The measuring configuration according to claim 1, wherein said measuring surface and said beam entry surface or said beam exit surface are formed from level surfaces aligned parallel to each other and/or that said elevation has an end surface constituting said measuring surface.

3. The measuring configuration according to claim 1, wherein said body is a mono-crystal made of $Al_2O_3$, $Y_3Al_5O_{12}$ or $MgAl_2O_4$.

4. The measuring configuration according to claim 1, wherein:
   at least one of said body or said elevation are formed centrally symmetrically in respect to an axis perpendicular to said measuring surface; and/or
   at least one of said measuring surface, said body or said elevation have at least two symmetry planes running perpendicular to said measuring surface.

5. The measuring configuration according to claim 1, wherein said elevation has a cylindrical, truncated cone-shaped form, a truncated pyramid-shaped form or a form of a rectangular cuboid with a regular polygonal base.

6. The measuring configuration according to claim 1, wherein said ledge has a crossover edge to said remaining part of said body or to a contact surface formed on said remaining part of said body, surrounding said elevation, said crossover edge is at least one of rounded or conical.

7. The measuring configuration according to claim 6, wherein said contact surface runs parallel to said measuring surface.

8. The measuring configuration according to claim 1, wherein said elevation has at least a circumferential surface, which departs from said measuring surface inclined outwards and with a contact surface formed on said remaining part contains an angle A of $45°≤A≤90°$, wherein the angle A opens to an interior of said elevation.

9. The measuring configuration according to claim 8, wherein said angle A is $70°≤A≤90°$.

10. The measuring configuration according to claim 1, wherein:
    said remaining part of said body is formed at least partially from a rotation body having a circumferential surface; and
    said beam conductive surfaces are formed from said circumferential surface or parts of said circumferential surface of said rotation body.

11. The measuring configuration according to claim 10, wherein said rotation body is selected from the group consisting of a spherical body and an ellipsoid body.

12. The measuring configuration according to claim 1, wherein said deflecting prism is used for performing at least one of refractometer measurements or attenuated ATR-measurements.

13. The measuring configuration according to claim 1, wherein:
    said elevation has a circumferential surface; and
    said wall has an inner wall section, said inner wall section of said wall connecting to said solder joint has a distance to said circumferential surface of said elevation, which exceeds a thickness of said solder joint between said elevation and said inner wall section.

14. The measuring configuration according to claim 13, wherein a distance between at least one sub-area of said inner wall section of said wall forming said solder joint to said at least one circumferential surface of said elevation exceeds a thickness of said solder joint between said elevation and said inner wall section, said at least one circumferential surface at least in sections continuously increases towards said measuring surface.

15. The measuring configuration according to claim 1, further comprising a layer made of titanium, gold, a titanium alloy or a gold alloy applied to a circumferential surface of said elevation in an area of said solder joint, said layer having a thickness of less than 100 μm.

16. The measuring configuration according to claim 1, wherein:
    said measuring unit having a housing; and
    said deflecting prism and said housing are exclusively connected via said solder joint.

17. The measuring configuration according to claim 1, wherein:
    said remaining part has a contact surface;
    said measuring surface has an inner wall section;
    said elevation has a circumferential surface; and
    a thickness of said solder joint or a distance between said circumferential surface of said elevation and said inner wall section of said measuring surface increases towards said contact surface.

18. The measuring configuration according to claim 1, wherein:
    said remaining part has a contact surface; and
    a height of said elevation in relation to said contact surface or said remaining part of said body and/or a width of said contact surface are selected so that a crossover edge does not influence a measuring beam path or lies outside the measuring beam path.

19. The measuring configuration according to claim 1, wherein said measuring surface extends over maximally 60% of said height of said elevation.

20. The measuring configuration according to claim 1, wherein said measuring surface is connected flatly level with an outer surface of said wall.

* * * * *